United States Patent
Perrey

(10) Patent No.: US 11,890,143 B2
(45) Date of Patent: Feb. 6, 2024

(54) ULTRASOUND IMAGING SYSTEM AND METHOD FOR IDENTIFYING CONNECTED REGIONS

(71) Applicant: GE Precision Healthcare LLC, Wauwatosa, WI (US)

(72) Inventor: Christian Perrey, Mondsee (AT)

(73) Assignee: GE Precision Healthcare LLC, Wauwatosa, WI (US)

(*) Notice: Subject to any disclaimer, the term of this patent is extended or adjusted under 35 U.S.C. 154(b) by 10 days.

(21) Appl. No.: 17/245,160

(22) Filed: Apr. 30, 2021

(65) Prior Publication Data

US 2022/0346755 A1    Nov. 3, 2022

(51) Int. Cl.
*A61B 8/08*    (2006.01)
*A61B 8/00*    (2006.01)

(52) U.S. Cl.
CPC .............. *A61B 8/5215* (2013.01); *A61B 8/08* (2013.01); *A61B 8/463* (2013.01)

(58) Field of Classification Search
None
See application file for complete search history.

(56) References Cited

U.S. PATENT DOCUMENTS

| | | | |
|---|---|---|---|
| 2017/0281094 A1* | 10/2017 | Ghaboussi | A61B 8/485 |
| 2019/0105013 A1 | 4/2019 | Wang | |
| 2020/0104997 A1* | 4/2020 | Takagi | G06T 7/215 |

FOREIGN PATENT DOCUMENTS

WO    WO-2021142267 A1 *    7/2021

OTHER PUBLICATIONS

Cunningham et al., "Real-Time Ultrasound Segmentation, Analysis and Visualisation of Deep Cervical Muscle Structure," (Feb. 2017), IEEE Transactions on Medical Imaging, vol. 36, No. 2, pp. 653-665. (Year: 2017).*
Van Sloun et al. "Zonal Segmentation in Transrectal Ultrasound Images of the Prostate Through Deep Learning," (Dec. 20, 2018) 2018 IEEE International Ultrasonics Symposium (IUS). (Year: 2018).*
Singhal et al., "Deep Learning Based Junctional Zone Quantification using 3D Transvaginal Ultrasound in Assisted Reproduction," (Jul. 2020) Annu Int Conf IEEE Eng Med Biol Soc, Jul. 2020, 2020:2133-2136. (Year: 2020).*
Singal et al., "Automated Assessment of Endometrium From Transvaginal Ultrasound Using Deep Learned Snake," (Jun. 19, 2017), 2017 IEEE 14th International Symposium on Biomedical Imaging (ISBI 2017). (Year: 2017).*

(Continued)

*Primary Examiner* — Joel Lamprecht
*Assistant Examiner* — Ashish S Jasani

(57) ABSTRACT

Various methods and systems are provided for identifying connected regions in ultrasound images. An exemplary method includes acquiring ultrasound video data of an anatomical region while a force is being applied to induce movement within the anatomical region, the ultrasound video data including a plurality of ultrasound images. The method includes identifying two or more connected regions in one of the plurality of ultrasound images, generating a modified ultrasound image by graphically distinguishing the first connected region from the second connected region, and causing a display device to display the modified image.

22 Claims, 10 Drawing Sheets

(56) References Cited

OTHER PUBLICATIONS

Leonardi et al., "Prevalence of negative sliding sign representing pouch of Douglas obliteration during pelvic transvaginal ultrasound for any indication," (Mar. 21, 2020), Ultrasound Obstet Gynecol2020;56: 928-933. (Year: 2020).*

Leonardi et al. ("UOG video abstract: Prevalence of negative sliding sign representing pouch of Douglas obliteration during pelvic transvaginal ultrasound for any indication,"(Dec. 1, 2020) <https://www.isuog.org/resource/uog-video-abstract-negative-sliding-sign-pouch-of-douglas-obliteration . . . > (Year: 2020).*

Ayachi et al., "Accuracy of preoperative real-time dynamic transvaginal ultrasound sliding sign in prediction of pelvic adhesions in women with previous abdominopelvic surgery: prospective, multicenter, double-blind study," (Mar. 13, 2017) Ultrasound in Obstetrics & Gynecology, vol. 51, issue 2. (Year: 2017).*

Hudelist et al. ,"Combination of transvaginal sonography and clinical examination for preoperative diagnosis of pelvic endometriosis, " (Feb. 6, 2009) Human Reproduction, vol. 24, Issue 5, May 2009, pp. 1018-1024. (Year: 2009).*

Guerriero et al., "Systematic approach to sonographic evaluation of the pelvis in women with suspected endometriosis, Including terms, definitions and measurements: a consensus opinion from the International Deep Endometriosis Analysis (IDEA) group," Jun. 28, 2016, https://doi.org/10.1002/uog.15955, 16 pages.

Leonardi et al., "How to perform an ultrasound to diagnose endometriosis," Apr. 22, 2018 https://doi.org/10.1002/ajum.12093, 9 pages.

Randall, "Towards a non-invasive diagnostic aid for abdominal adhesions using dynamic MRI and image processing," (2017) PhD thesis, University of Sheffield, 273 pages.

* cited by examiner

ULTRASOUND IMAGING SYSTEM AND METHOD FOR IDENTIFYING CONNECTED REGIONS

FIELD OF THE INVENTION

The subject matter disclosed herein relates generally to ultrasound imaging systems and methods for identifying connected regions in an ultrasound image and displaying a modified ultrasound image that graphically distinguishes a first connected region from a second connected region.

BACKGROUND OF THE INVENTION

Ultrasound imaging has been shown to be a useful tool for screening patients for endometriosis. According to conventional techniques, a clinician applies pressure to the patient in order to cause one or more organs within the patient to move with respect to other organs. The clinician acquires real-time ultrasound images while applying pressure in order to observe how organs move with respect to each other. For example, it is common for clinicians to evaluate how the anterior rectum glides over the posterior vaginal wall and/or the posterior cervix, or to evaluate how the anterior rectosigmoid glides over the posterior uterus/upper fundus. Studies have shown that there is a relationship between how freely these organs glide over each other and the likelihood of a patient having bowel endometriosis. If a patient has bowel endometriosis, adhesions are often present between organs which inhibits the ability of the organs to glide smoothly across one another in response to the applied pressure. For example, if the anterior rectum does not glide smoothly over the posterior vaginal wall and/or the posterior cervix, or the anterior rectum does not glide smoothly over the posterior uterus/upper fundus, the patient is considered to have a negative sliding sign. If the anterior rectum glides smoothly over the posterior vaginal wall and/or the posterior cervix and the anterior rectum glides smoothly over the posterior uterus/upper fundus, the patient is considered to have a positive sliding sign. Having a negative sliding sign is correlated with a diagnosis of bowel endometriosis. As such, performing an ultrasound imaging procedure to determine a patient's sliding sign has become an accepted screening technique for bowel endometriosis.

Accurately determining the sliding sign may be difficult for a clinician. As described above, it is necessary for the clinician to apply pressure with either his/her hand or the ultrasound probe in order to observe how the organs glide/slide with respect to each other. It may be difficult for the clinician to accurately determine whether or not a specific organ is gliding smoothly with respect to other adjacent organs or showing signs of adhesion. As discussed previously, it is necessary for the clinician to apply the pressure necessary to cause the organs to slide, hold the probe in the appropriate position to acquire the desired ultrasound images, and evaluate the acquired ultrasound images to determine if the images exhibit a negative sliding sign or a positive sliding sign. It can be challenging even for experienced clinicians to accurately determine the sliding sign of a patient. For at least the reasons discussed hereinabove, there is a need for improved methods and ultrasound imaging systems for graphically distinguishing connected regions within an ultrasound image in order to make the determination of a patient's sliding sign easier and more accurate.

BRIEF DESCRIPTION

In an embodiment, a method includes acquiring with an ultrasound probe, ultrasound video data of an anatomical region while a force is being applied to induce movement within the anatomical region, where the ultrasound video data comprises a plurality of ultrasound images. The method includes identifying, with a processor, two or more connected regions in one of the plurality of ultrasound images, the two or more connected regions including a first connected region and a second connected region, where each of the two or more connected regions represents an interconnected tissue group that moves as a unit in response to a force. The method includes generating, with the processor, a modified ultrasound image based on the one of the plurality of ultrasound images by graphically distinguishing the first connected region from the second connected region. The method includes causing, with the processor, a display device to display the modified ultrasound image.

In an embodiment, an ultrasound imaging system includes an ultrasound probe, a display device, and a processor in electronic communication with the ultrasound probe and the display device. The processor is configured to control the ultrasound probe to acquire ultrasound video data of an anatomical region while a force is being applied to induce movement within the anatomical region, where the ultrasound video data includes a plurality of ultrasound images. The processor is configured to identify two or more connected regions in one of the plurality of ultrasound images, the two or more connected regions including a first connected region and a second connected region, where each of the two or more connected regions represents an interconnected tissue group that moves as a unit in response to the force. The processor is configured to automatically generate a modified ultrasound image based on the one of the plurality of images by graphically distinguishing the first connected region from the second connected region. The processor is configured to cause the display device to display the modified ultrasound image.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
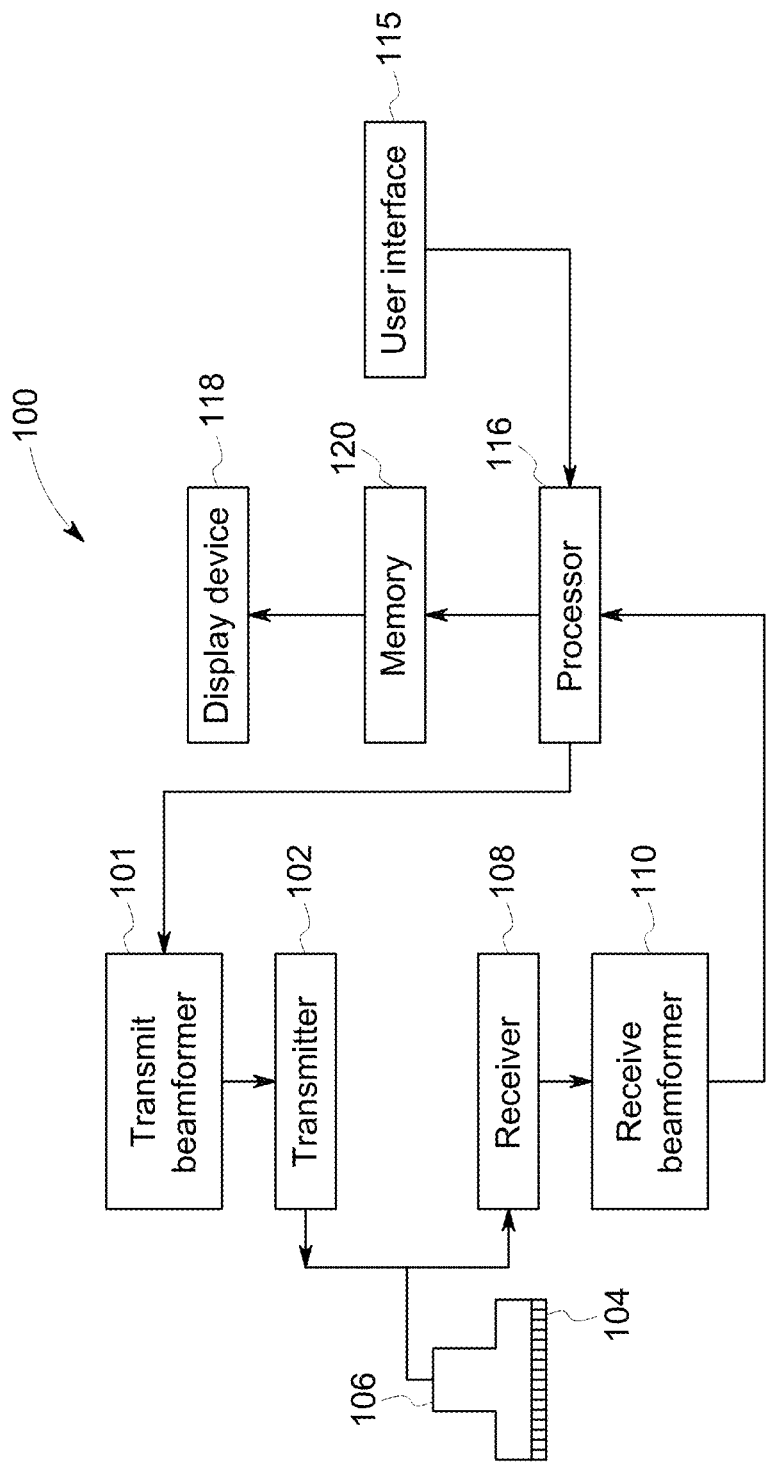
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a body (not shown) through one or more transmit events. The elements 104 may be arranged in an array. The ultrasound probe 106 may be linear array probe, a curved linear array probe, a phased array probe, a curved phased array probe, a 4D matrix array probe, or any other type of ultrasound probe. According to some exemplary embodiments, the ultrasound probe 106 may be a transvaginal probe or an abdominal probe. Still referring to FIG. 1, the pulsed ultrasonic signals are back-scattered from structures in the body, like blood cells or muscular tissue, to produce echoes that return to the elements 104. The echoes are converted into electrical signals by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the ultrasound probe 106. The terms "scan" or "scanning" may also be used in this disclosure to refer to acquiring data through the process of transmitting and receiving ultrasonic signals. The ultrasound probe 106 may be controlled to acquire ultrasound video data, which includes a plurality of ultrasound images. According to an embodiment, ultrasound video data may include a plurality of ultrasound images, or frames, that are each acquired at a different time. The ultrasound video data may be viewed as a video or cine in order to provide the clinician with information about how various structures in the patient move with respect to each other. The ultrasound video data may be displayed during the time of the acquisition in a live or real-time imaging session, or the ultrasound video data may be stored in a memory and viewed at a later time in a retrospective session.

A user interface 115 may be used to control operation of the ultrasound imaging system 100. The user interface 115 may be used to control the input of patient data, or to select various modes, operations, parameters, and the like. The user interface 115 may include one or more user input devices such as a keyboard, hard keys, a touch pad, a touch screen, a track ball, rotary controls, sliders, soft keys, or any other user input devices.

The ultrasound imaging system 100 also includes a processor 116 to control the transmit beamformer 101, the transmitter 102, the receiver 108 and the receive beamformer 110. The user interface 115 is in electronic communication with the processor 116. The processor 116 may include one or more separate hardware components, such as a central processing unit (CPU), a microprocessor, a microcontroller, a graphics processing unit (GPU), a digital signal processor (DSP), combinations thereof, and the like. According to some embodiments, the processor 116 may include one or more GPUs, where some or all of the GPUs include a tensor processing unit (TPU). According to embodiments, the processor 116 may include a field-programmable gate array (FPGA), or any other type of hardware capable of carrying out processing functions. The processor 116 may be an integrated component or it may be distributed across various locations. For example, according to an embodiment, processing functions associated with the processor 116 may be split between two or more processors based on the type of operation. For example, embodiments may include a first processor configured to perform a first set of operations and a second, separate processor to perform a second set of operations. According to embodiments, the processor 116 may be configured to implement a machine-learning model. The processor 116 may be configured to execute instructions accessed from a memory. For example, the instructions may be stored on a non-transitory computer readable medium configured for execution by the processor 116. According to an embodiment, the processor 116 is in electronic communication with the ultrasound probe 106, the receiver 108, the receive beamformer 110, the transmit beamformer 101, and the transmitter 102. For purposes of this disclosure, the term "electronic communication" may be defined to include both wired and wireless connections. The processor 116 may control the ultrasound probe 106 to acquire ultrasound data, such as ultrasound video data. The processor 116 controls which of the elements 104 are active and the shape of a beam emitted from the ultrasound probe 106. The processor 116 is also in electronic communication with a display device 118, and the processor 116 may process the ultrasound data into images for display on the display device 118. According to embodiments, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The ultrasound data, such as ultrasound video data, may be processed in real-time during a scanning session as the echo signals are received. The processor 116 may be configured to scan-convert the ultrasound data acquired with the ultrasound probe 106 so it may be displayed as one or more ultrasound images on the display device 118. Displaying ultrasound data in real-time may involve displaying the ultrasound data without any intentional delay. For example, the processor 116 may display each updated image frame as soon as each updated image frame of ultrasound data has been acquired and processed for display during a real-time imaging acquisition. Real-time frame rates may vary based on the size of the region or volume from which data is acquired and the specific parameters used during the acquisition. The processor 116 may also be configured to display each updated image frame in near real-time. For the purposes of this disclosure, the term "near real-time" will be defined to be mean performing an operation within 10 seconds. For example, displaying a modified ultrasound image based on an ultrasound image in near real-time would entail displaying the modified ultrasound image within 10 second from the time when the ultrasound image was acquired. In many embodiment, near real-time operations will be performed significantly faster than within 10 seconds. For example, many near real-time operations will be performed within 2 seconds.

According to other embodiments, the data may be stored temporarily in a buffer (not shown) during a scanning session and processed in less than real-time, or retrospectively. According to embodiments that include a software beamformer, the functions associated with the transmit beamformer 101 and/or the receive beamformer 108 may be performed by the processor 116.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending the size of each frame of data and the parameters associated with the specific application. For example, many applications involve acquiring ultrasound data at a frame rate of about 50 Hz. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

In various embodiments of the present invention, ultrasound data may be processed by other or different mode-related modules by the processor 116 (e.g., B-mode, color Doppler, M-mode, color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processing module may be provided that reads the image frames from a memory, such as the memory 120, and displays the image frames in real-time or near real-time while a procedure is being carried out on a patient. The video processing module may store the image frames in an image memory, from which the images are read and displayed.

Figure 2:
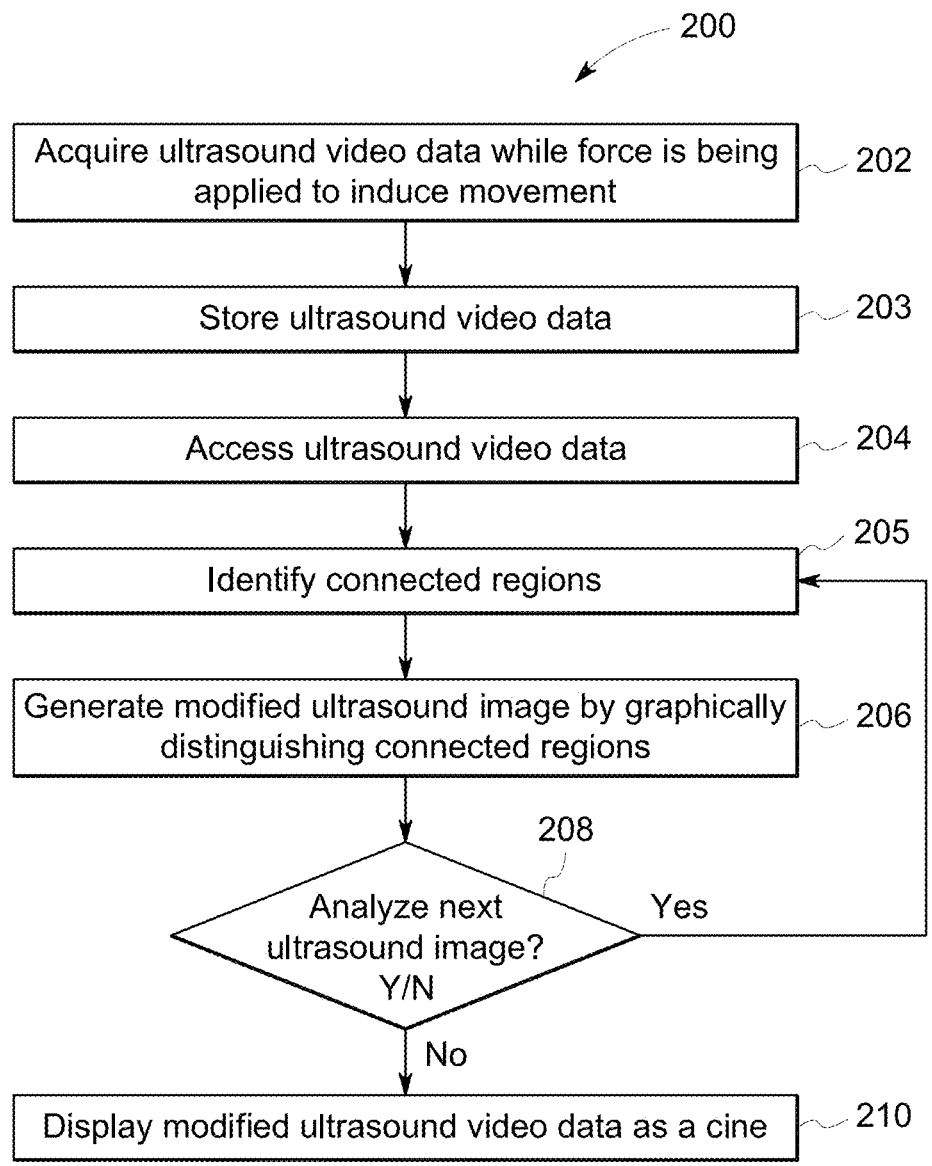
FIG. 2 is a flow chart in accordance with an embodiment.

FIG. 2 illustrates a flowchart of one embodiment of a method 200 for analyzing an ultrasound image for connected regions. The method 200 shown in FIG. 2 may be performed with the ultrasound imaging system 100 shown in FIG. 1. The technical effect of the method 200 is the generation and display of modified ultrasound video data in order to graphically distinguish connected regions.

At step 202, the processor 116 controls the ultrasound probe 106 to acquire ultrasound video data while a force is being applied to induce movement. In the process of controlling the ultrasound probe 106 to acquire ultrasound video data, the processor 116 also controls the transmit beamformer 101, the transmitter 102, the receiver 108 and the receive beamformer 110. At step 203, the processor 116 stores the ultrasound video data in a memory such as the memory 120.

Acquiring ultrasound video data includes acquiring a plurality of ultrasound images at different points in time. The ultrasound video data may be processed/displayed as it is acquired in either a real-time or a near real-time process, or the ultrasound video data may be stored and accessed for processing and/or displaying retrospectively. The ultrasound video data may be stored in a memory, such as the memory 120, or, according to other embodiments, the ultrasound video data may be stored in a storage device that is not part of the ultrasound imaging system 100. The ultrasound video data may, for instance, be stored in a non-local storage device, such as on a server or other storage device on either a local or a remote network.

Next at step 204, the processor 116 accesses the stored ultrasound video data from memory, such as the memory 120. At step 205, the processor 116 identifies two or more connected regions in one of the plurality of ultrasound images. The processor 116 may be configured to automatically identify the two or more connected regions, or the processor 116 may be configured to semi-automatically identify the two or more connected regions. In an embodiment, the processor 116 may be configured to receive at least one user input in order to help constrain the locations of one or more of the connected regions or a boundary between the connected regions. For example, the processor 116 may be configured to receive an input through the user interface 115 designating one or more connected regions or a boundary between two adjacent connected regions. The user may, for example, click on each suspected connected region, or use a user interface device to move a cursor along a suspected boundary between two adjacent connected regions. Other embodiments may be configured to receive different types of input through the user interface 115 in order to help identify the connected regions at step 205.

Figure 3:
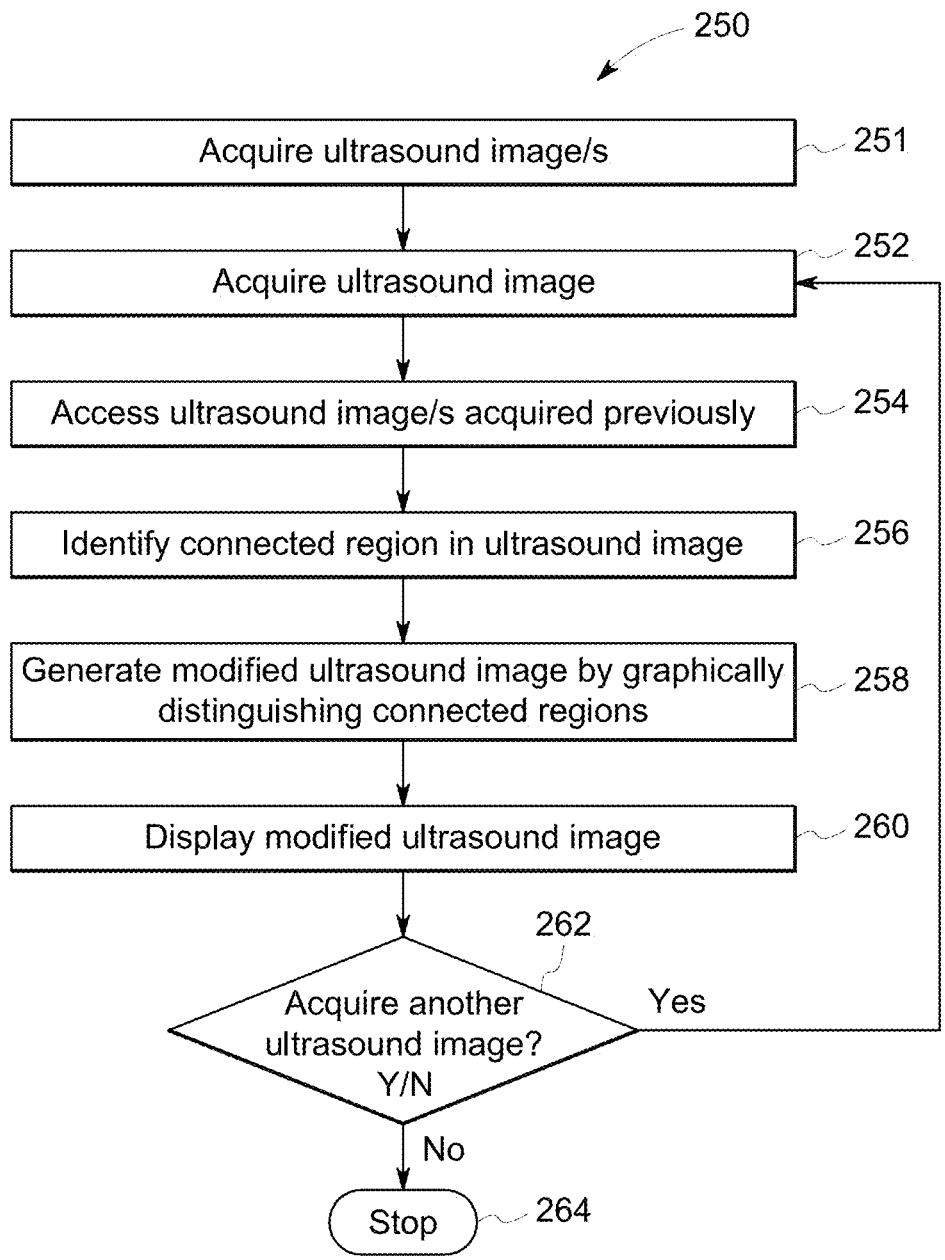
FIG. 3 is a flow chart in accordance with an embodiment.
Figure 4:
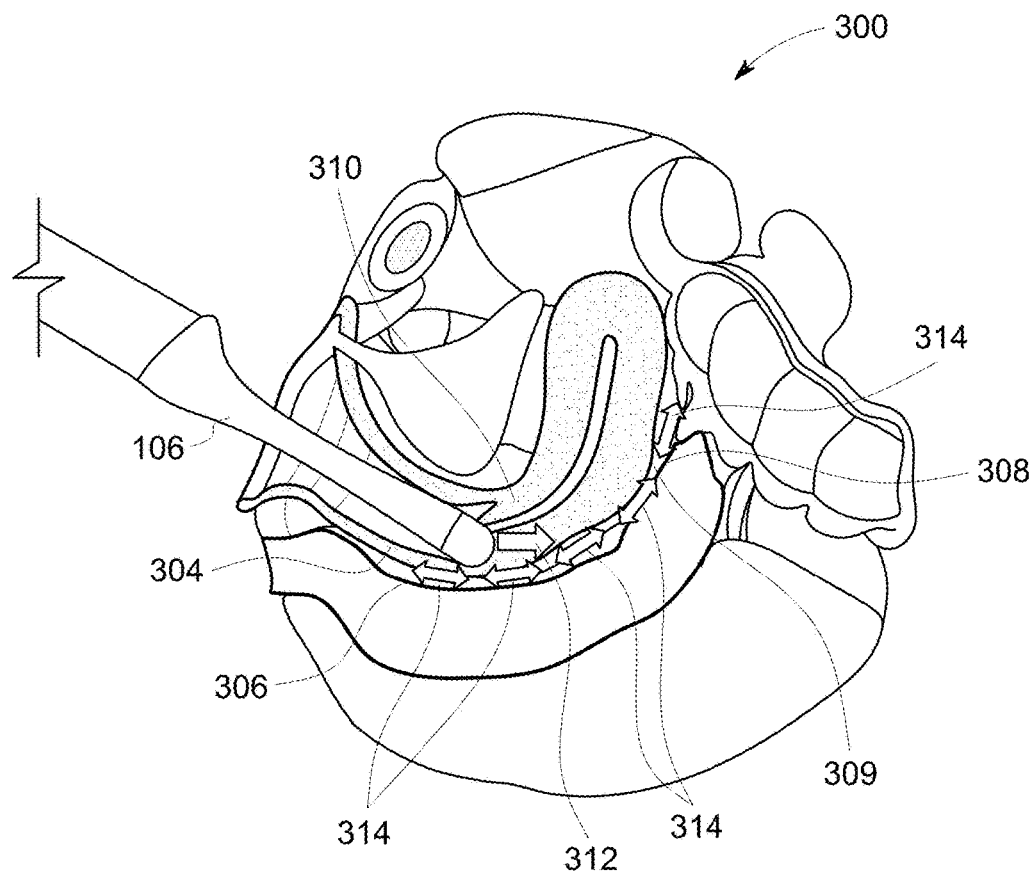
FIG. 4 is a representation of a cross-section of a patient's abdomen during an ultrasound scan in accordance with an embodiment.

FIG. 4 is a is a representation of a cross-section of a patient's abdomen 300 during an ultrasound scan in accordance with an embodiment. The representation of the patient's abdomen 300 includes the ultrasound probe 106. The ultrasound probe 106 is represented as a transvaginal probe in accordance with an embodiment in FIG. 4. The representation of the patient's abdomen 300 includes a posterior vaginal wall 304, an anterior rectal wall 306, an anterior rectosigmoid wall 308, a posterior uterus wall 309, a cervix 310, a directional arrow 312, and a plurality of bi-directional arrows 314. FIG. 3 will be described in accordance with an embodiment where a force is applied to the cervix 310 in a direction aligned with the directional arrow 312 in order to induce movement within the patient's abdomen during the process of acquiring the ultrasound video data. Applying a force to the cervix 310 may be used to determine whether or not the anterior rectal wall 306 glides smoothly over the posterior vaginal wall 304. According to an embodiment, the force applied to the cervix 310 in a direction aligned with the directional arrow 312 may be varied so there are periods of increasing force and periods of decreasing force during the acquisition of the ultrasound video data.

Figure 5:
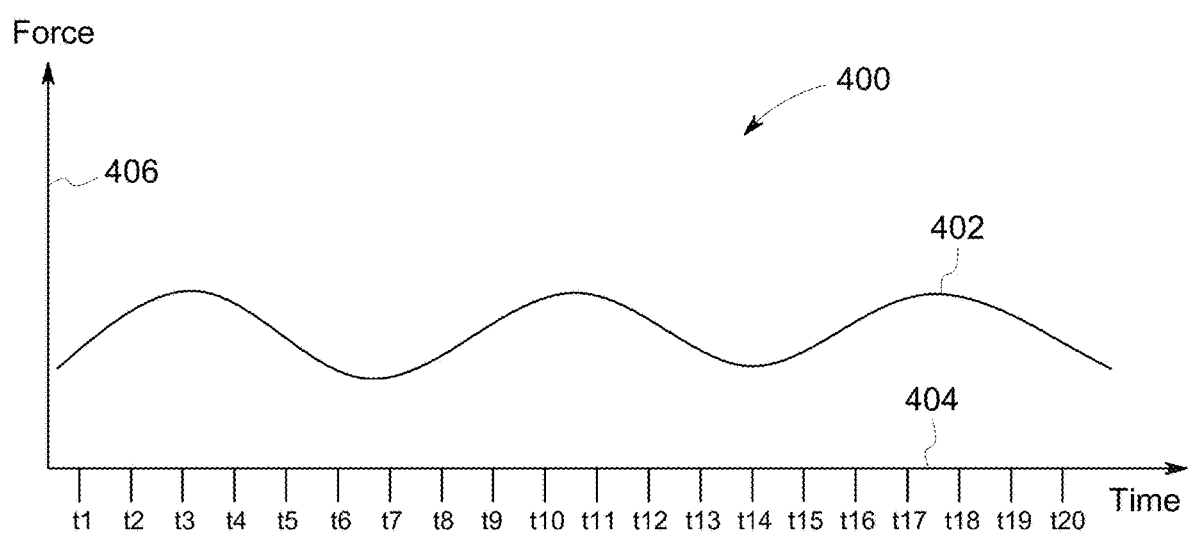
FIG. 5 is a graph of force versus time in accordance with an embodiment.

FIG. 5 is a graph of force versus time in accordance with an embodiment. The graph represents the force or pressure applied to the patient in order to induce movement with an anatomical region being scanned during the process of acquiring the ultrasound video data. FIG. 4 illustrates an example where the force is applied to the cervix 310 by the ultrasound probe 106 in order to induce movement within the patient's abdomen. According to other embodiments, the clinician may apply the force to the patient in a different location using the ultrasound probe 106, and/or the clinician may use his/her hand or another instrument in order to apply the force in a different location and/or direction. For example, the clinician may use his/her hand to apply force or pressure to the patient's uterus from a location exterior to the patient. The clinician may, for example, apply pressure to the patient's lower abdomen in a direction towards the patient's spine in order to determine whether or not the anterior rectosigmoid wall 308 glides smoothly over the posterior uterus wall 309. The clinician may apply the force to induce movement within the patient in other patterns according to various embodiments.

At step 202 of the method 200, the processor 116 controls the ultrasound probe 106 to acquired ultrasound video data of an anatomical region while a force is being applied to induce movement within the anatomical region. FIG. 4 shows an example of an anatomical region and the clinician may apply the force using either the ultrasound probe 106 or a portion of his/her hand. The force may, for example, be applied in a manner consistent with the graph shown in FIG. 5. It should be appreciated by those skilled in the art that the force that is applied in order to induce movement may be applied in other patterns and/or in other locations according to various embodiments. The ultrasound video data includes a plurality of ultrasound images, which may also be called "frames" for purposes of this application. Each ultrasound image, or frame, is acquired at a different time in order to acquire the ultrasound video data.

The graph 400 shown in FIG. 5 will be used to demonstrate how the processor 116 may control the ultrasound probe 106 to acquire ultrasound video data of an anatomical region while force is being applied to induce movement in the anatomical region in accordance with an exemplary embodiment. The force may be applied in a manner to induce one or more anatomical structures to move relatively with respect to each other. FIG. 5 shows a graph 400 with a curve 402 showing force versus time. An x-axis 404 represents time and a y-axis 406 represents force. The graph 400 is labeled with times t1, t2, t3, t4, t5, t6, t7, t8, t9, t10, t11, t12, t13, t14, t15, t16, t17, t18, t19, and t20 along the x-axis 404. The processor 116 may control the ultrasound probe 106 to acquire an ultrasound image or frame at each of these times. For example, the processor 116 may control the ultrasound probe 106 to acquire a first frame at time t1, a second frame at time t2, a third frame at time t3, a fourth frame at time t4, etc. As shown by the curve 402, the force applied to induce movement varies from time t1 to time t20. The force applied to induce movement within the anatomical region is varied according to a roughly sinusoidal pattern in FIG. 5, but it should be understood that the force may be applied according to other patterns to induce movement. Referring to the curve 402, the force applied at time t1 is different from the force applied at time t2, and the force applied at time t3 is different than the force applied at time t1 or time t2. Since the force is intended to induce movement in the anatomical region, and the amount of the force that is applied is varied during the acquisition of the ultrasound video data, the ultrasound images acquired at times t1, t2, t3, . . . t20 should therefore represent the structures within the anatomical region at different relative positions in at least some of the ultrasound images.

At step 205, the processor 116 identifies connected regions in one of the plurality of ultrasound images acquired at step 202. In order to accurately identify the connected regions in one of the plurality of ultrasound images, it is anticipated that the processor 116 will need to analyze at least one ultrasound image acquired before the one of the plurality of ultrasound images. According to an exemplary embodiment, it is anticipated that the processor 116 will analyze a plurality of ultrasound images acquired before the one of the plurality of images in order to identify the connected image in the one of the plurality of images.

For example, in order to identify the connected regions in the ultrasound image acquired at time t6, the processor 116 may analyze the ultrasound images acquired at time t5, time t4, time t3, time t2, and time t1; in order to identify the connected region in the ultrasound image acquired at time t7, the processor 116 may analyze the ultrasound images acquired at time t6, time t5, time t4, time t3, and time t2; and so forth. While FIG. 4 is being described according to an exemplary embodiment where the 5 most-recently acquired frames are used to identify the connected regions in an ultrasound image, other embodiments may use a different number of frames to identify the connected regions. For example, some embodiments may use fewer than five frames (for example, the four most-recently acquired frames, the three most-recently acquired frames, etc.) and other embodiments may use more than 5 most-recently acquired frames (for example, the 6 most-recently acquired frames, the 7 most-recently acquired frames, etc.) to identify the connected regions. Embodiments may also use the current frame in addition to one or more previously acquired frames to identify the connected regions.

In order to identify a sliding sign of the patient, it is necessary to determine if individual structures in the anatomical region are sliding smoothly over each other in response to the force being applied or if the individual structures are all sliding as one interconnected structure. As described previously, having the individual structures slide smoothly over one another indicates a positive sliding sign while having the individual structures move as one interconnected structure indicates a negative sliding sign.

The clinician applies the force, such as in the manner represented by the curve 402, while acquiring the ultrasound video data. The force is intended to induce movement within the anatomical region. If the individual structures are not interconnected to each other, then the different frames of the ultrasound video data will show each structure smoothly sliding over the adjacent structures in response to the force being applied while acquiring the ultrasound video data. However, if there are adhesions, such as from bowel endometriosis or any other condition, each individual structure will not slide smoothly over the adjacent structures in response to the force being applied while acquiring the ultrasound video data.

The processor 116 may be configured to identify one or more connected regions in one of the ultrasound images by analyzing multiple ultrasound images in the ultrasound video data. The processor 116 analyzes the multiple ultrasound images in order to identify one or more connected regions in the ultrasound image based on how the structures represented in the data move in response to the force applied to induce movement within the anatomical region. Each connected region represents an interconnected tissue group that moves as a unit in response to the force. Different portions of the connected region may move a different amount in response to the force due to compression of the tissue and/or drag caused by friction or interference from surrounding tissues. In a patient with a positive sliding sign, each connected region may represent a single organ or structure. Each individual organ or structure represents an interconnected tissue group that moves as a unit in response to the force. However, in patients with bowel endometriosis or other conditions that cause structures around the patient's uterus to become physically interconnected. For example, bowel endometriosis can cause bands of scar tissue called adhesions to form between various organs or tissues in the abdomen in the volume generally near to the patient's uterus. The adhesions physically cause the various organs or structures to become stuck to each other. Two or more organs or structures that are stuck together will move as a unit in response to the force applied to induce movement within the anatomical region. The number of individual connected regions will vary based on the anatomy of the patient being scanned, any underlying conditions of the patient being scanned, and the size of the field-of-view from which the ultrasound video data was acquired at step 202. In a patient with significant adhesions between organs, it is possible for two or more of the organs and tissues within the field-of-view of the ultrasound video data to be physically interconnected. If there are adhesions connecting all of the organs and tissues represented in the ultrasound image, then the processor 116 may only detect a single connected region. On the other hand, if two or more of the organs or tissues within the field-of-view of the ultrasound video do not have adhesions, then the processor 116 may identify two of more separate connected regions at step 205.

The processor 116 may use image processing techniques and/or implement a machine-learning model in order to identify the connected regions in the ultrasound image. As discussed above, it is anticipated that it will be necessary for the processor 116 to analyze at least two frames/ultrasound images from the ultrasound video data in order to identify the two or more connected regions. It is necessary to analyze at least two frames in order to identify connected regions based on the movement of structures represented in the ultrasound images from frame-to-frame within the ultrasound video data. Since a force was applied to induce movement during the acquisition of the video data, the processor 116 needs to compare at least two frames acquired at different times in order to identify regions in each ultrasound image that move as a connected region. According to exemplary embodiments, it may be desirable to analyze considerably more than two frames in order to have a more frames showing the motion of the anatomical region captured in the ultrasound video data. The processor 116 may use image processing techniques, such as speckle tracking, motion detection, object localization, segmentation, motion field analysis, or any other image processing technique to identify relative motion of structures within the ultrasound video data. For example, the processor 116 may be configured to use speckle tracking in order to determine relative motion between the various adjacent frames of the ultrasound video data in order to identify connected regions in one of the ultrasound images. The processor 116 may be configured to analyze speckle tracking data obtained over multiple frames of the ultrasound video data to determine if the various segmented structures or organs are moving independently or as one interconnected structure in response to the applied force. The processor 116 may apply a segmentation algorithm to segment structures or organs from multiple images in the ultrasound video data in order to determine if the various segmented structures or organs are moving independently or as one interconnected structure in response to the applied force. The processor 116 may use motion field analysis to determine the relative motions of a plurality of points or pixels within the ultrasound image over a plurality of adjacent frames. Based on the motion field analysis, the processor 116 may compare the relative motions of various points or pixels over multiple frames of the ultrasound video data in order to identify connected regions in the ultrasound image. The processor 116 may be configured to use a threshold regarding differences in relative motion between the various points or pixels within each of the plurality of images in order to identify the connected regions. For example, the processor 116 may only consider points or pixels to be included within a connected structure if they have less than a certain percentage of difference in the amount of relative motion in response to the applied force. The processor 116 may be configured to use any other type of image processing technique to identify one or more connected regions in the ultrasound image.

According to an embodiment, the processor 116 may be configured to use artificial intelligence in order to identify the connected regions during step 205. For example, the processor 116 may be configured to implement a machine-learning model, i.e., a model trained through machine learning techniques, in order to detect the connected regions during step 206. The processor 116 may, for instance implement a machine-learning model, such as a random decision forest, a support vector machine, a logistic regression, a neural network, or any other machine learning model to detect the connected regions. According to an exemplary embodiment, the processor 116 may be configured to implement a machine-learning model in order to identify connected regions within a plurality of ultrasound images that are part of ultrasound video data. The machine-learning model (e.g., the random decision forest, the support vector machine, the logistic regression, the neural network, etc.) may be trained using training data during either supervised or unsupervised learning before the machine-learning model is implemented by the processor to identify the connected regions. Embodiments may utilize two or more different types of machine-learning models in order to identify the connected regions during step 206.

Figure 6:
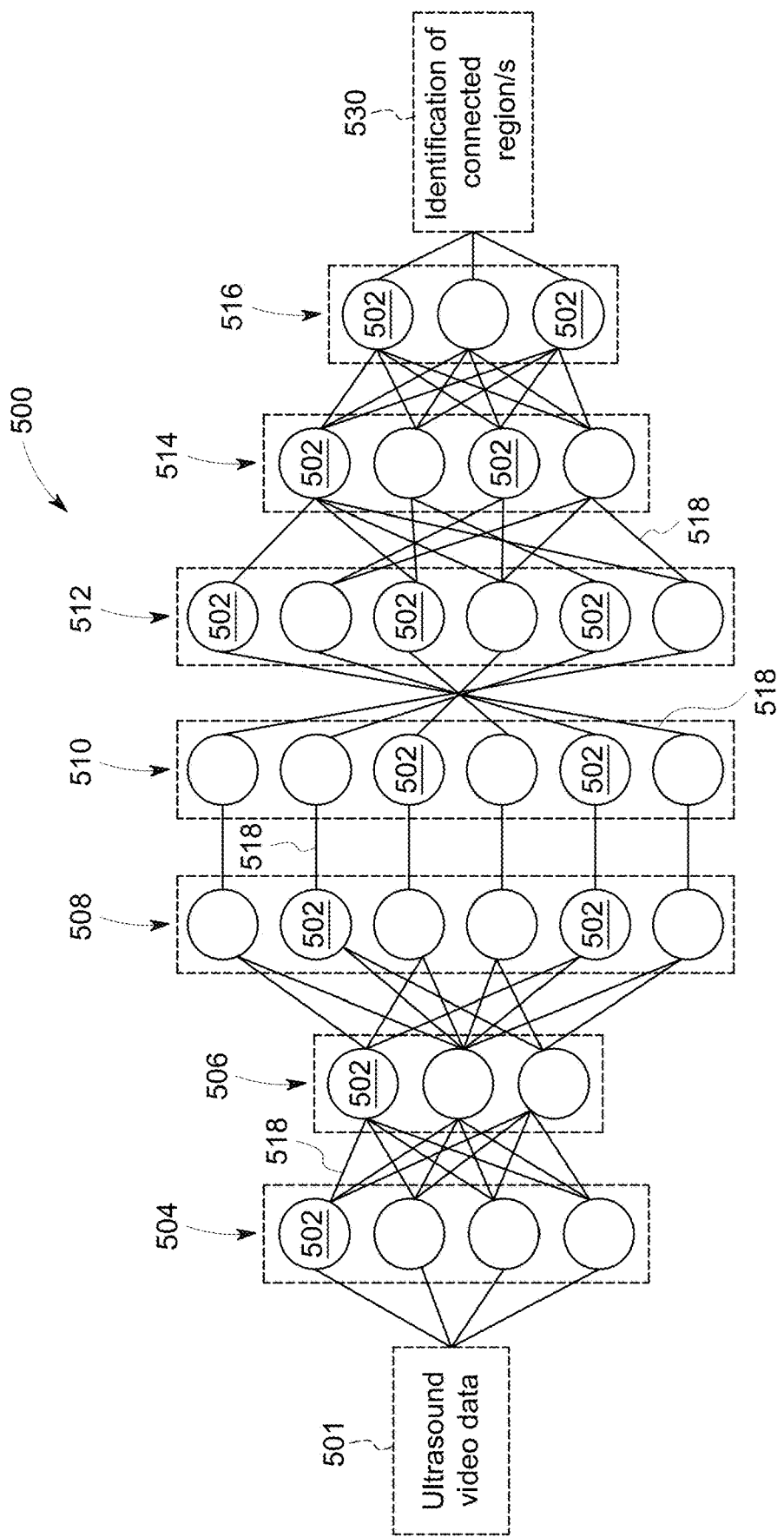
FIG. 6 is a schematic diagram of a neural network in accordance with an embodiment.

According to an exemplary embodiment, the machine-learning model may be a neural network. The processor 116 may be configured to implement the neural network in order to identify the connected regions at step 205. FIG. 6 depicts a schematic diagram of a neural network 500 having one or more nodes/neurons 502 which, in some embodiments, may be disposed into one or more layers 504, 506, 508, 510, 512, 514, and 516. Neural network 500 may be a deep neural network. As used herein with respect to neurons, the term "layer" refers to a collection of simulated neurons that have inputs and/or outputs connected in similar fashion to other collections of simulated neurons. Accordingly, as shown in FIG. 5, neurons 502 may be connected to each other via one or more connections 518 such that data may propagate from an input layer 504, through one or more intermediate layers 506, 508, 510, 512, and 514, to an output layer 516. The one or more intermediate layers 506, 508, 510, 512, and 514 are sometimes referred to as "hidden layers."

Figure 7:
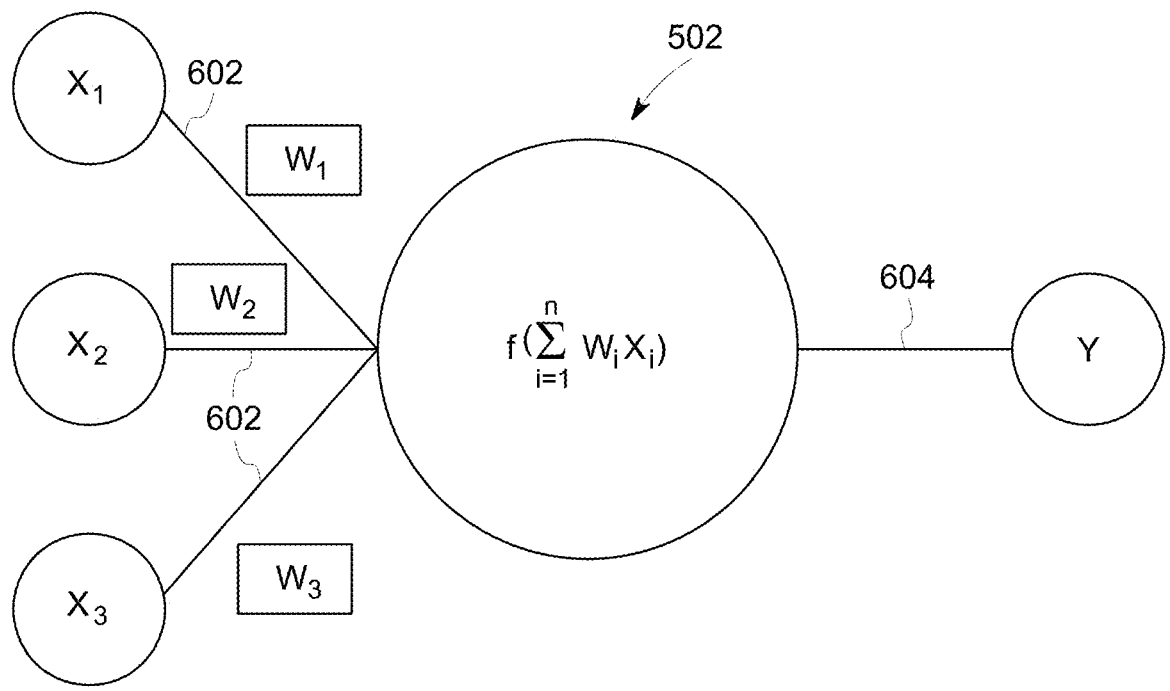
FIG. 7 is a schematic diagram showing input and output connections for a neuron of a neural network in accordance with an embodiment.

FIG. 7 shows input and output connections for a neuron in accordance with an exemplary embodiment. As shown in FIG. 7, connections (e.g., 518) of an individual neuron 502 may include one or more input connections 602 and one or more output connections 604. Each input connection 602 of neuron 502 may be an output connection of a preceding neuron, and each output connection 604 of neuron 502 may be an input connection of one or more subsequent neurons. While FIG. 7 depicts neuron 502 as having a single output connection 604, it should be understood that neurons may have multiple output connections that send/transmit/pass the same value. In some embodiments, neurons 502 may be data constructs (e.g., structures, instantiated class objects, matrices, etc.), and input connections may be received by neuron 502 as weighted numerical values (e.g., floating point or integer values). For example, as further shown in FIG. 7, input connections X1, X2, and X3 may be weighted by weights W1, W2, and W3, respectively, summed, and sent/transmitted/passed as output connection Y. As will be appreciated, the processing of an individual neuron 502 may be represented generally by the equation:

$$Y = f\left(\sum_{i=1}^{n} W_i X_i\right)$$

where n is the total number of input connections 602 to neuron 502. In one embodiment, the value of Y may be based at least in part on whether the summation of $W_i X_i$ exceeds a threshold. For example, Y may have a value of zero (0) if the summation of the weighted inputs fails to exceed a desired threshold.

As will be further understood from FIGS. 6 and 7, input connections 602 of neurons 502 in input layer 504 may be mapped to an input 501, while output connections 604 of neurons 502 in output layer 516 may be mapped to an output 530. As used herein, "mapping" a given input connection 602 to input 501 refers to the manner by which input 501 affects/dictates the value said input connection 602. Similarly, as also used herein, "mapping" a given output connection 604 to output 530 refers to the manner by which the value of said output connection 604 affects/dictates output 530.

Accordingly, in some embodiments, the acquired/obtained input 501 is passed/fed to input layer 504 of neural network 500 and propagated through layers 504, 506, 508, 510, 512, 514, and 516 such that mapped output connections 604 of output layer 516 generate/correspond to output 530. As shown, input 501 may include ultrasound video data. The ultrasound video data may include one or more connected regions. The output 530 may include the identification of one or more connected regions identified based on the ultrasound video data.

Neural network 500 may be trained using a plurality of training datasets. According to various embodiments, the neural network 500 may be trained with ultrasound video data. Each training dataset may include ultrasound video data that are, for example, annotated. Based on the training datasets, the neural network 500 may learn to identify connected structures from the video data. The deep learning (due to, for example, identifiable trends in placement, size, etc. of anatomical features) may cause weights (e.g., W1, W2, and/or W3) to change, input/output connections to change, or other adjustments to neural network 500. Further, as additional training datasets are employed, the machine learning may continue to adjust various parameters of the neural network 500 in response. As such, a sensitivity of the neural network 500 may be periodically increased, resulting in a greater accuracy of connected region identification. It should be appreciated by those skilled in the art that the neural network 500 is an exemplary neural network and that the other types and configurations of neural networks may be used according to various embodiments. For example, neural networks with a different number of layers, such as a different number of "hidden layers" may be used in various embodiments.

Next, at step 206, the processor 116 is configured to generate a modified ultrasound image by graphically distinguishing the connected regions identified during step 204. The processor 116 may generate the modified ultrasound image by color-coding each of the identified connected regions with a different color. For example, according to an embodiment with two connected regions identified at step 205, the modified ultrasound image may graphically distinguish the connected regions by colorizing pixels within the first connected region with a first color and colorizing pixels within the second connected region with a second color that is different than the first color. According to an embodiment, the processor 116 may use a semi-transparent overlay in order to colorize the modified ultrasound image to graphically distinguish the different connected regions. According to another embodiment, the processor 116 may graphically distinguish the connected regions that were identified in the ultrasound image by displaying a boundary line between adjacent connected regions. For example, according to an embodiment with two connected regions, the processor 116 may display a boundary line between a first connected region and a second connected region in order to help the clinician to distinguish the various connected regions while viewing the modified ultrasound image. According to embodiments, the processor 116 may graphically distinguish the connected regions identified at step 204 using two or more different techniques. For example, the processor 116 may graphically distinguish a first connected region from a second connected region by both color-coding the connected regions so the first connected region is colorized with a different color than the second connected region and displaying a boundary line in between the first connected region and the second connected region. Additional details about some exemplary modified ultrasound images will be provided hereinafter.

As discussed above, at step 206, the processor 116 modifies the one of the plurality of ultrasound images in order to graphically distinguish or identify each of the connected regions identified at step 205. Next, at step 208, the processor 116 determines if it is desired to analyze the next ultrasound image in the ultrasound video. The processor 116 may, for example, determine if all the ultrasound images in the ultrasound video data have been analyzed at step 205. If there are still ultrasound images in the ultrasound video data to analyze, the method returns to step 205. Step 205, step 206, and step 208 may be performed as many time as required. The processor 116 may be configured to access the next ultrasound image in the ultrasound video data each time the method 200 iteratively repeats steps 205, 206, and 208. If it is not desired to analyze the next ultrasound image, the method 200 advances to step 210.

At step 210, the processor 116 controls the display device 118 to display each of the modified ultrasound images generated at step 206 as a cine, or video loop. According to an embodiment, the processor 116 may generate modified ultrasound video data based on all the modified ultrasound images generated at step 206. Each of the modified ultrasound images may, for example, be placed in the same order in the modified ultrasound video data as a corresponding ultrasound image of the ultrasound video data. At step 210, the processor may display the modified ultrasound video data as a cine or video loop. The modified ultrasound video data therefore includes a plurality of modified ultrasound images that were each generated at step 206. The connected regions, which represent an interconnected tissue group that moves as a unit in response to a force, are graphically distinguished in each of the modified ultrasound images. As such, when displaying the modified ultrasound video data to the clinician as a cine at step 210, it is easy for the clinician to visually distinguish the connected regions. By visually distinguishing the connected regions in the modified ultrasound images, the method 200 enables the clinician to easily determine if a patient is exhibiting a negative sliding sign or a positive sliding sign. As discussed previously, a negative sliding sign is correlated with a diagnosis of endometriosis. As such, the method 200 may be used in order to screen for conditions such as endometriosis, or more specifically, for bowel endometriosis.

FIG. 3 illustrates a flowchart of one embodiment of a method 250. The method 250 shown in FIG. 3 may be performed with the ultrasound imaging system 100 shown in FIG. 1. The technical effect of the method 250 is the generation and display of modified ultrasound images in order to graphically distinguish connected regions.

At step 251, the processor 116 control the ultrasound probe 106 to acquire one or more ultrasound images. According to an exemplary embodiment, the one or more ultrasound images acquired at step 251 may be acquired during the process of acquiring ultrasound video data.

At step 252, the processor 116 controls the ultrasound probe 106 to acquire an ultrasound image. The ultrasound image acquired at step 252 may also be acquired during the process of acquiring ultrasound video data. Next, at step 254, the processor accesses one or more ultrasound images acquired before the ultrasound image acquired at step 252. During the first iteration of the method 250, the one or more images accessed at step 252 may be acquired at step 251. According to an exemplary embodiment, the ultrasound image acquired at step 252 and the one or more ultrasound images accessed at step 254 may all be acquired as part of ultrasound video data. Additionally, the one or more ultrasound images accessed at step 254 may be the preceding one or more ultrasound images (i.e. frames) that were acquired as part of the ultrasound video data at step 251. For example, the processor 116 may access either a fixed number of frames acquired before the ultrasound image acquired at step 252 or the processor 116 may access ultrasound images acquired over a fixed amount of time before the acquisition of the ultrasound image at step 252. In other words, if the ultrasound image acquired at step 252 is image frame N in an acquisition of ultrasound video data, the ultrasound images accessed at step 254 may include image frame N−1, image frame N−2, image frame N−3, image frame N−4, etc. While not shown on the flowchart represented in FIG. 3, the ultrasound video data acquired at step 251 and 252 is acquired while a force is being applied to induce movement within an anatomical region being imaged. The force may be applied with the ultrasound probe 106, the clinician's hand, or any other instrument in a similar way to that which was described with respect to the method 200. The force is intended to induce movement within the anatomical region being imaged and may be varied over time in order to induce movement that will result in organs within the anatomical region moving during the acquisition of the ultrasound video data.

At step 256, the processor 116 identifies one or more connected regions in the ultrasound image acquired at step 252. The processor 116 may identify the one or more connected regions using image processing techniques or by implementing a machine-learning model according to any of the techniques described with respect to the method 200. The processor 116 may be configured to automatically identify the two or more connected regions, or the processor 116 may be configured to semi-automatically identify the two or more connected regions. In an embodiment, the processor 116 may be configured to receive at least one user input in order to help constrain the locations of one or more of the connected regions or a boundary between the connected regions. For example, the processor 116 may be configured to receive an input through the user interface designating one or more connected regions or a boundary between two adjacent connected regions. The user may, for example, click on each suspected connected region, or use a user interface device to move a cursor along a suspected boundary between two adjacent connected regions. Other embodiments may be configured to receive different types of input through the user interface 115 in order to help identify the connected regions at step 256.

Next, at step 258, the processor 116 generates a modified ultrasound image by graphically distinguishing the connected regions. The modified ultrasound image is based on the ultrasound image acquired at step 252. The processor 116 may graphically distinguish the one or more connected regions in the ultrasound image through any of the techniques described in this document, including color-coding each connected region with a different color and/or displaying a boundary line between a first connected region and a second connected region. The boundary line may include a plurality of different color-coded segments, where each of the plurality of color-coded segments is colorized to represent an amount of relative movement between the first connected region and the second connected region at the location of each particular color-coded segment.

At step 260, the processor 116 displays the modified ultrasound image based on the ultrasound image acquired at step 252. For example, the processor 116 may control the display device 118 to display the modified ultrasound image. As discussed previously, the modified ultrasound image is modified to graphically distinguish each of the one or more connected regions identified in the ultrasound image acquired at step 252.

Next, at step 262, the processor 116 determines if it is desired to acquire another ultrasound image. If it is desired to acquire another ultrasound image, the method 250 returns to step 252. The method 250 may iteratively repeat steps 252, 254, 256, 258, 260 and 262 as long as it is desired to acquired additional ultrasound images at step 262. According to an embodiment, the processor 116 may be configured to iteratively repeat steps 252, 254, 256, 258, 260 and 262 as long as the clinician continues to acquire ultrasound data with the ultrasound probe 106. According to another embodiment, the processor 116 may be configured to iteratively repeat steps 252, 254, 256, 258, 260 and 262 as long as ultrasound data is being acquired and the ultrasound imaging system 100 remains in a mode intended to identify connected regions. The ultrasound imaging system may automatically enter the mode based on a particular workflow, or the ultrasound imaging system 100 may manually enter the mode to identify the connected region in response to a user input entered through the user interface 115.

The processor 116 may be configured to access a different set of previously acquired ultrasound images during each iteration of performing steps 252, 254, 256, 258, 260 and 262. As described previously, during the first iteration, the processor 116 may access ultrasound images acquired at step 251 while performing step 254. However, while performing step 254 during subsequent iterations, the processor 116 may access previously acquired ultrasound images acquired at step 252 during previous iterations of performing steps 252, 254, 256, 258, 260 and 262 either instead of or in addition to the ultrasound image/s acquired at step 251. For example, it is intended that the processor 116 will access ultrasound images acquired before the ultrasound image being analyzed at step 256 in order to identify the connected regions since the processor 116 is using a number of the previously acquired ultrasound images/frames acquired while a force is being applied in order to induce movement to identify the connected regions.

Those skilled in the art should appreciate that performing multiple iterations of steps 252, 254, 256, 258, 260 and 262 will result in the display of an updated modified ultrasound image at step 260 during each iteration of performing steps 252, 254, 256, 258, 260 and 262. According to an embodiment, performing multiple iterations of steps 252, 254, 256, 258, 260 and 262 may result in the displaying of modified ultrasound images as a video or cine. The collection of modified ultrasound images may be considered to be modified ultrasound video data, where each modified ultrasound image is a frame within the modified ultrasound video data. It should also be appreciated that according to an exemplary embodiment, the force applied to induce movement may be varied during the process of iteratively performing the steps 252, 254, 256, 258, 260 and 262. If it is not desired to acquire another ultrasound image at step 262, the method 250 advances to step 264 and stops. According to an embodiment, the processor 116 may control the ultrasound imaging system to enter a different imaging mode or the processor 116 may control the ultrasound probe 106 to stop acquiring ultrasound images at step 264.

Figure 8:
FIG. 8 is a representation of an ultrasound image in accordance with an embodiment.
Figure 9:
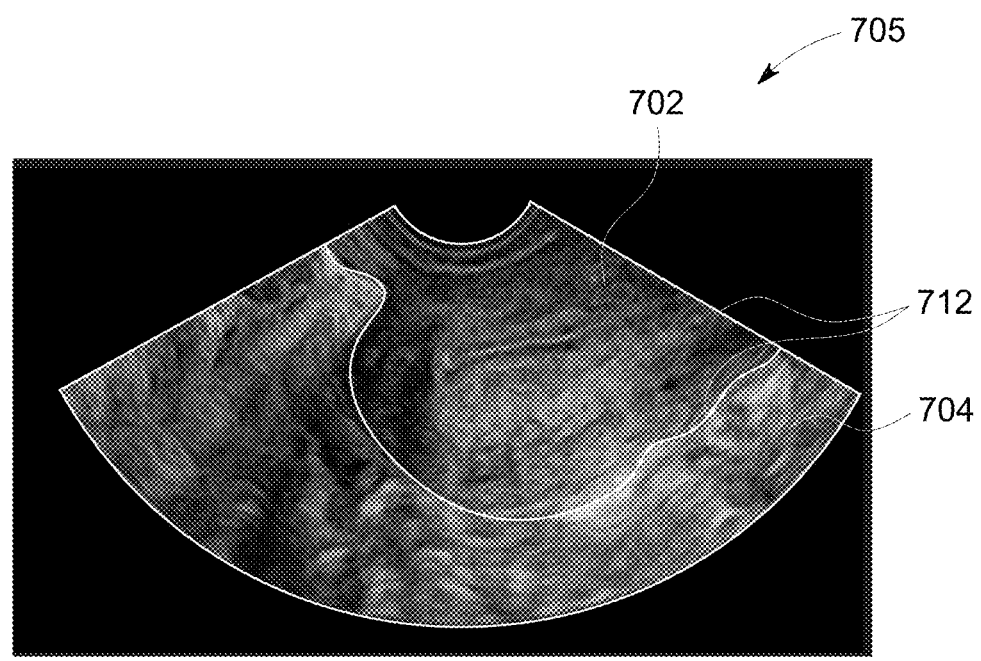
FIG. 9 is a representation of a modified ultrasound image in accordance with an embodiment.

FIG. 8 is a representation of an ultrasound image 700 in accordance with an embodiment. The ultrasound image 700 represents an ultrasound image such as that which would be acquired at step 202 or 252. FIG. 9 is a representation of a modified ultrasound image 705 including boundaries 712 to illustrate a first connected region 702 and a second connected region 704. The modified ultrasound image 705 is generated by adding the boundary lines 712 to the ultrasound image 700 shown in FIG. 8.

Figure 10:
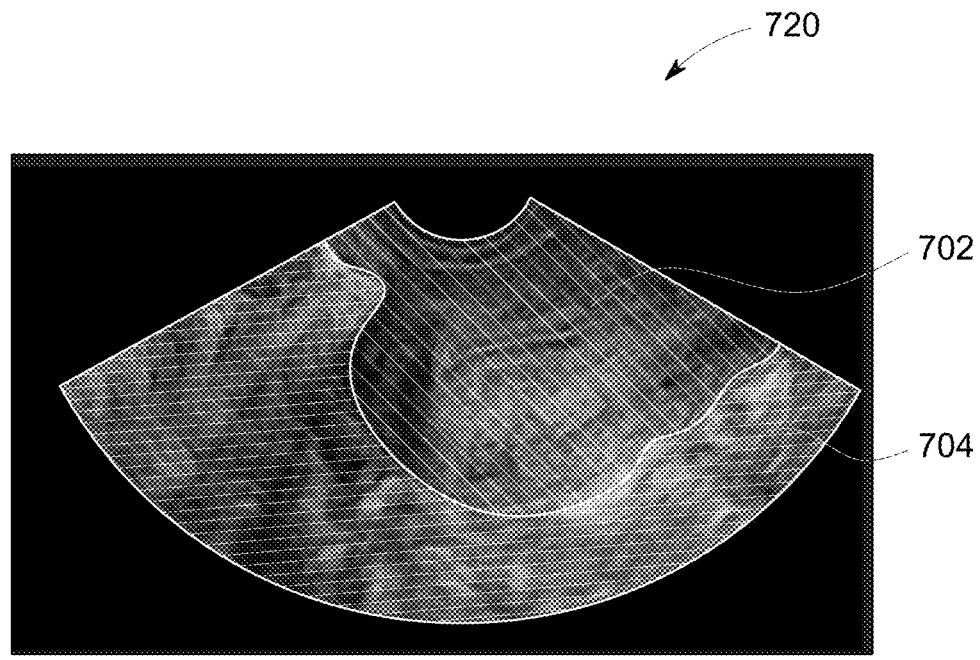
FIG. 10 is a representation of a modified ultrasound image in accordance with an embodiment.

FIG. 10 is a representation of a modified ultrasound image 720 in accordance with an embodiment. The modified ultrasound image 720 is an example of a modified ultrasound image that may be generated and displayed according to either the method 200 or the method 250. FIG. 8 includes the first connected region 702 and the second connected region 704. The processor 116 may be configured to color-code each of the connected regions identified in the modified ultrasound image 720. For example, the first connected region 702 may be colored or colorized using a first color and the second connected region 704 may be colored or colorized using a second color that is different than the first color as indicated by the lining on FIG. 10. According to an embodiment, the processor 116 may be configured to display the color as an overlay on the ultrasound image 700. For example, the processor 116 may blend the colors used to identify the first connected region 702 and the second connected region 704 with the information in the ultrasound image 700 to provide the effect of colorizing the ultrasound image 700. This way, the information in the ultrasound image 700 is still readily visible to users viewing the modified ultrasound image 720.

Figure 11:
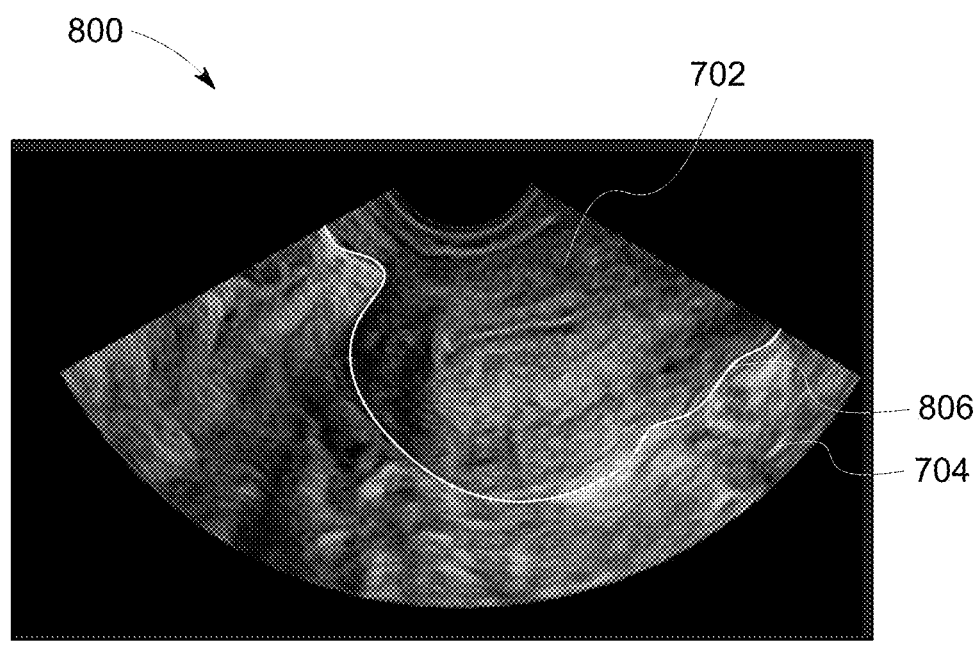
FIG. 11 is a representation of a modified ultrasound image in accordance with an embodiment.

FIG. 11 is a representation of a modified ultrasound image 800 in accordance with an embodiment. The modified ultrasound image 800 is an example of a modified ultrasound image that may be generated and displayed according to either the method 200 or the method 250. The modified ultrasound image 800 includes the first connected region 702 and the second connected region 704. The processor 116 graphically distinguishes the first connected region 702 from the second connected region 704 by displaying a boundary line 806 between the first connected region 702 and the second connected region 704.

Figure 12:
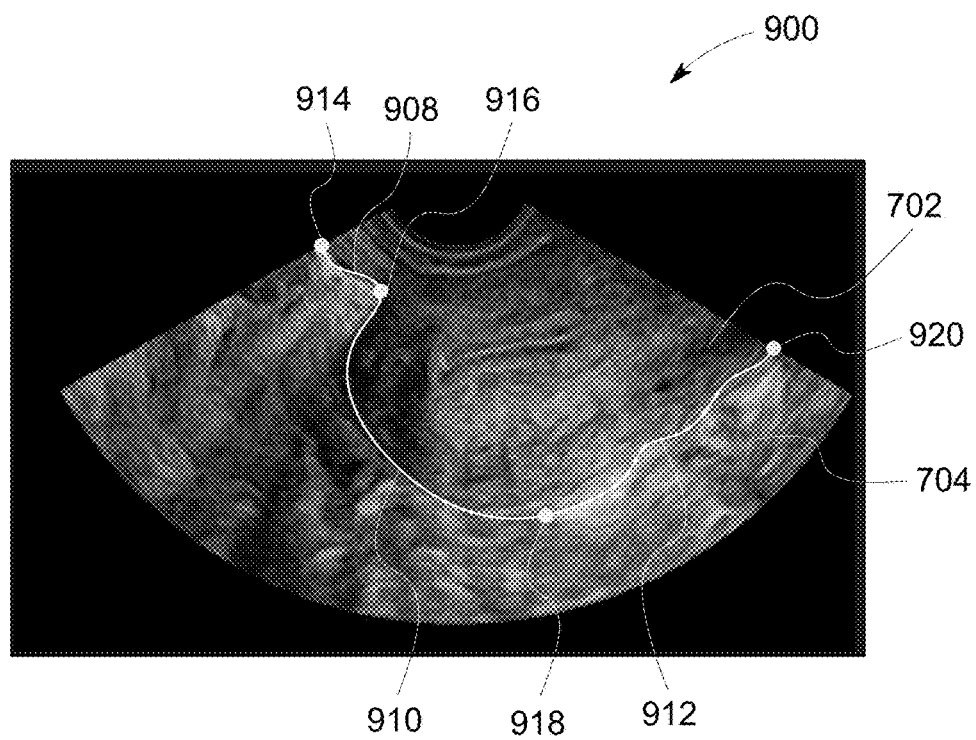
FIG. 12 is a representation of a modified ultrasound image in accordance with an embodiment.

FIG. 12 is a representation of a modified ultrasound image 900 in accordance with an embodiment. The modified ultrasound image 900 is an example of a modified ultrasound image that may be generated and displayed according to either the method 200 or the method 250. The modified ultrasound image 900 includes the first connected region 702 and the second connected region 704. The processor 116 graphically distinguishes the first connected region 702 from the second connected region 704 by displaying a boundary line between the first connected region 702 and the second connected region 704. The boundary line shown in FIG. 9 has 3 segments: a first segment 908, a second segment 910, and a third segment 912. The first segment 908 extends between point 914 and point 916; the second segment 910 extends between point 916 and point 918; and the third segment extends between point 918 and point 920. The first segment 908 may be displayed in a first color to represent a first level of relative movement between the first connected region 702 and the second connected region 704; the second segment 910 may be displayed in a second color to represent a second level of relative movement between the first connected region 702 and the second connected region 704; and the third segment 912 may be displayed in a third color to indicate a third level of relative movement between the first connected region 702 and the second connected region 704. The points displayed on FIG. 9 are placed in order to more easily described the segments in the boundary line. Various embodiments may not display the points shown on FIG. 9 while displaying a boundary line including two or more segments that are color-coded based on the motion between adjacent connected regions. According to other embodiments, the number of segments on the boundary line may be less than three or greater than three. Embodiments may include two or more different techniques to graphically distinguish the first connected region from the second connected region. For example, the modified image may include both color-coding, as shown in FIG. 10, and a boundary line, as shown in FIG. 12.

The method 200, shown in FIG. 2, results in the display of modified ultrasound video data as a cine on the display device 118. Likewise, in the method 250, shown in FIG. 3, iteratively repeating steps 252, 254, 256, 258, 260 and 262 may result in the display of a modified ultrasound video data as a cine. It should be appreciated that the processor 116 may graphically distinguish the connected region/s differently in various frames of the modified ultrasound video data in both method 200 and method 250. For example, the connected region/s in each frame, or modified ultrasound image, may be a different shape and/or location due to the force that was applied to induce movement during the acquisition of the ultrasound video data. Likewise, the processor 116 may adjust the way that the connected regions are graphically distinguished to reflect the size and shape of the connected regions in the current ultrasound image. The processor 116 may be configured to display the modified ultrasound video data according to the method 250 in near real-time, since there is a small delay introduced due to the processing required in order to identify the connected region at each iteration of step 256 and generate the modified ultrasound image at each iteration of step 258. The method 200 displays each modified ultrasound image retrospectively after the acquisition of the ultrasound video data since previously-acquired ultrasound video data is accessed from a memory at step 204.

Figure 13:
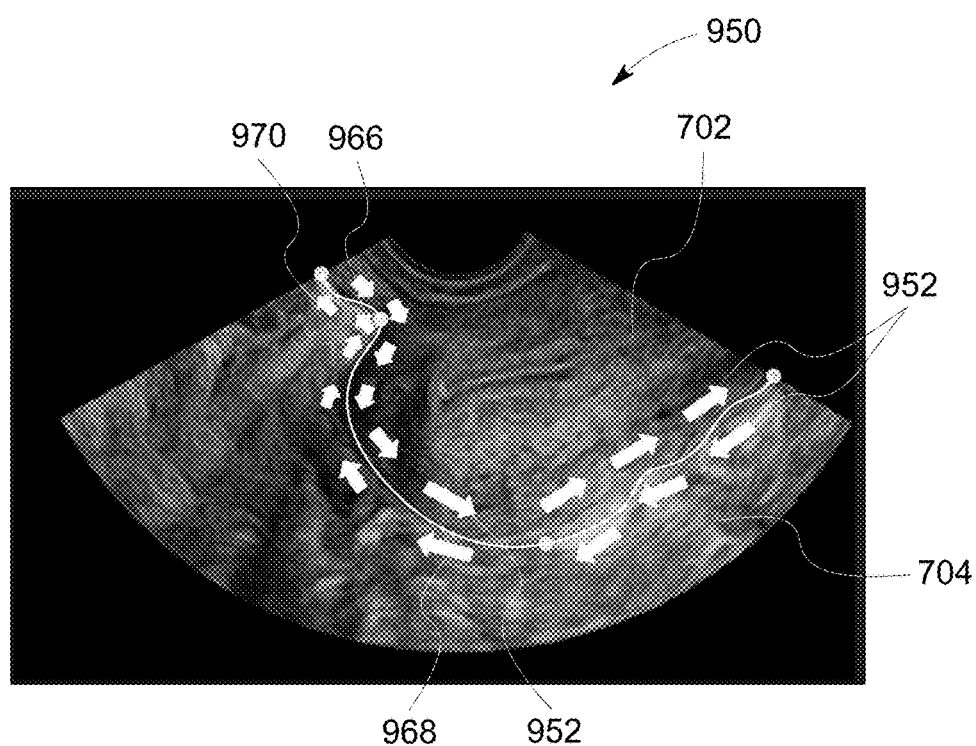
FIG. 13 is a representation of a modified ultrasound image in accordance with an embodiment.

According to an embodiment, the processor 116 may be configured to determine a direction of motion between a first connected segment and a second connected segment for a plurality of different locations. FIG. 13 is a modified ultrasound image 950 in accordance with an embodiment. The modified ultrasound image 950 includes a plurality of icons 952 in order to graphically represent the direction of motion between the first connected region 702 and the second connected region 704. Each of the icons 952 shown in FIG. 13 is an arrow. The size of the arrow represents the amount of relative movement at a particular location and the direction of the arrow represents the direction of the movement. For example, a first arrow 966 is smaller than a second arrow 968. Additionally, the first arrow 966 is pointed in a different direction than the second arrow 968. A third arrow 970 is generally similar in size to the first arrow 966, but pointed in a different direction. This indicates the that magnitude of the motion at the locations indicated by the first arrow 966 and the second arrow 968 are generally similar by that the motion is in different directions. In the embodiment shown in FIG. 13, each of the arrows 962 represents the direction and magnitude of the relative motion between the first connected region 702 and the second connected region 704 for the tissue underneath the arrow. The arrows may also be colorized in order to convey the magnitude or the direction of the motion. For example, the arrows shown in FIG. 13 may be colorized based on the general direction of the tissue motion. All of the arrows in the first connected region 702 are colorized with a first color to indicate that the tissue is generally moving in a left-to-right direction and all of the arrows in the second connected region 704 are colorized with a second color to indicate that the tissue is generally moving in a right-to-left direction. According to embodiments the arrows 952 may be colorized based on the magnitude of the relative movement between the first connected region 702 and the second connected region 704. It is to be appreciated that the processor 116 may be configured to update the icons, such as the arrows for every frame or only after a certain number of frames while displaying the modified ultrasound images as a cine. While arrows are shown in FIG. 13, according to other embodiments, different types of graphical icons may be used to graphically illustrate the magnitude and direction of the relative motion between the first connected region 702 and the second connected region 704 in other embodiments.

According to other embodiments, the processor 116 may be configured to use color to indicate the direction and magnitude of the relative motion between various connected regions. For example, the processor 116 may use colorized sub-regions to indicate the direction and magnitude of the motion in each of the modified ultrasound images. Conventional Color Flow Doppler imaging uses color to indicate the direction of flow and the magnitude of flow as determined by pulsed-wave Doppler. Color Flow Doppler imaging uses a first color (typically red) to indicate flow towards the ultrasound probe and a second color (typically blue) to indicate flow away from the ultrasound probe. Additionally, the intensity of the color used in Color Flow Doppler imaging indicates the velocity of the flow, with higher velocities conventionally indicated with greater intensities of the color (i.e., blue or red, according to convention).

Figure 14:
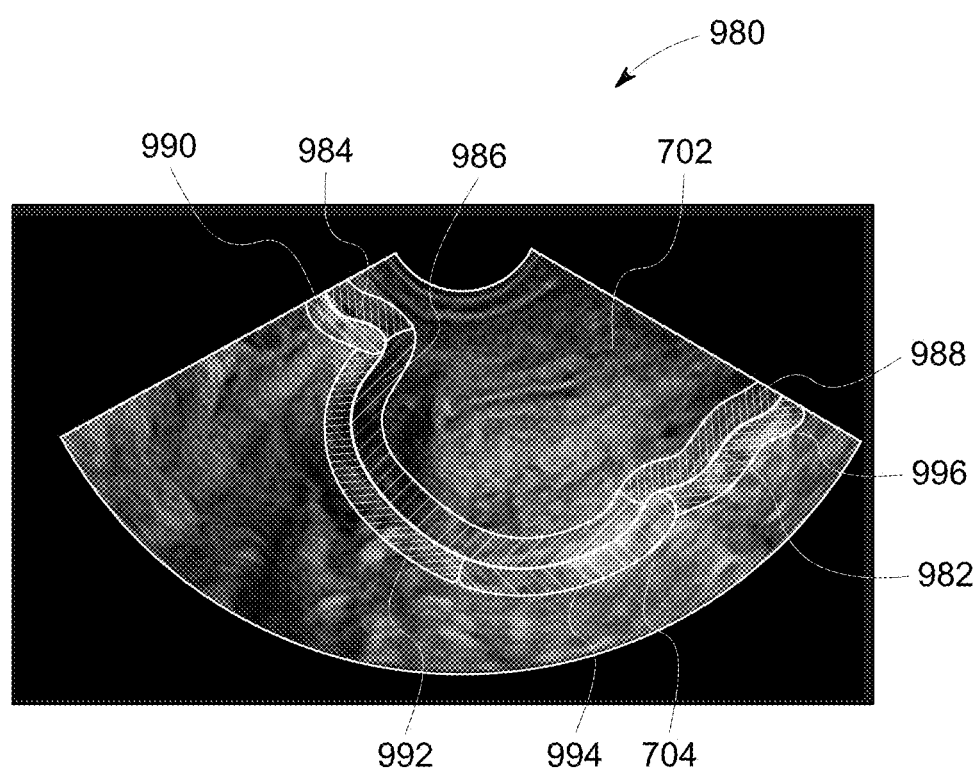
FIG. 14 is a representation of a modified ultrasound image in accordance with an embodiment.

FIG. 14 is a representation of a modified ultrasound imaging 980 in according to an embodiment. The modified ultrasound image 980 includes a boundary line 982 between the first connected region 702 and the second connected region 704. The modified ultrasound image 980 includes a first colorized region 984, a second colorized region 986, a third colorized region 988, a fourth colorized region 990, a fifth colorized region 992, a sixth colorized region 994, and a seventh colorized region 996. In a somewhat similar manner to that typically used in conventional Color Flow Doppler imaging, the processor 116 may use color to represent the magnitude and the direction of movement between the first connected region 702 and the second connected region 704. For example, the first colorized region 984 and the second colorized region 988 may both be displayed in the same color and the second colorized region 986 may be displayed in a different color as represented by the lining. The fourth colorized region 990 and the sixth colorized region 994 are displayed in the same color, and the fifth colorized region 992 and the seventh colorized region 996 are displayed in the same color as represented by the lining. According to an embodiment, the processor 116 may determine the direction of movement parallel to the boundary line 982 and display the colorized regions to represent the relative motion within the first connected region 702 with respect to the second connected region 704. The processor 116 may use either different colors, as shown in FIG. 14 or different intensities of the same color to indicate different velocities of movement between the first connected region 702 and the second connected region 704. For example, the first colorized region 984, the second colorized region 986, and the third colorized region 988 are all moving in a first direction along the boundary line 982 since they are all part of the first connected region 702. The fourth colorized region 990, the fifth colorized region 992, the sixth colorized region 994, and the seventh colorized region 996 are all moving in the second, opposite, direction along the boundary line 982 since they are all part of the second connected region 704. Color or intensity may be used to graphically display the direction and velocity of movement for the colorized regions. According to an embodiment, the processor 116 may only colorize a portion of the image within a specific distance of the boundary line 982. In other embodiments, the boundary line 982 may not be displayed at the same time as the colorized regions.

FIG. 9, FIG. 10, FIG. 11, FIG. 12, FIG. 13, and FIG. 14 each represent an example of a modified ultrasound image based on the ultrasound image 700 shown in FIG. 8 according to various embodiments for illustrative purposes. It is anticipated that the processor 116 would generate a plurality of modified ultrasound images for display as a cine or video. Each modified ultrasound image may be based on a different ultrasound image acquired from a different point in time. It is anticipated that sizes and shapes of the connected regions in each modified ultrasound image may be different based on the force being applied to the anatomical region during the acquisition of the ultrasound video data. Displaying the modified ultrasound images as a cine or video provides the clinician with feedback regarding the size and shape of any connected regions in the patient and how each connected region is moving with respect to other connected regions in the anatomical region being imaged. This in turn may be used to determine the patient's sliding sign of the patient.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of ultrasound imaging, comprising:
    acquiring, with an ultrasound probe, ultrasound video data of an anatomical region while an external force is being applied to induce movement within the anatomical region, where the ultrasound video data comprises a plurality of ultrasound images;
    designating, with a processor, two or more connected regions in one of the plurality of ultrasound images and a boundary between the two or more connected regions, the two or more connected regions including a first connected region and a second connected region, where each of the two or more connected regions represents an interconnected tissue group that moves as a unit in response to the external force;
    generating, with the processor, a modified ultrasound image based on the one of the plurality of ultrasound images, by graphically distinguishing the first connected region from the second connected region; and
    causing, with the processor, a display device to display the modified ultrasound image,
    wherein the first connected region is an anterior rectal wall of the anatomical region and the second connected region is a posterior vaginal wall of the anatomical region.

2. The method of claim 1, wherein said graphically distinguishing the first connected region from the second connected region comprises color-coding each of the two or more connected regions with a different color.

3. The method of claim 2, wherein the first connected region is graphically distinguished from the second connected region by adding a boundary line between the first connected region and the second connected region.

4. The method of claim 1, wherein the first connected region is graphically distinguished from the second connected region by adding a boundary line between the first connected region and the second connected region.

5. The method of claim 4, wherein the boundary line includes a plurality of color-coded segments including a first segment displayed in a first color to represent a first amount of relative movement between the first connected region and the second connected region and a second segment displayed in a second color to represent a second amount of relative movement between the first connected region and the second connected region, where the second color is different than the first color, and where the second amount of relative movement is greater than the first amount of relative movement.

6. The method of claim 1, wherein said designating the two or more connected regions in one of the plurality of images comprises analyzing two or more of the plurality of ultrasound images.

7. The method of claim 1, wherein the processor is configured to implement a machine-learning model to designate the two or more connected regions.

8. The method of claim 1, further comprising determining, with the processor, a direction of motion between the first connected region and the second connected region for a plurality of different locations; and performing at least one of:
    using color on the modified image to indicate the direction of motion for the plurality of different locations; or
    displaying a plurality of icons on the modified image to indicate the direction of motion for the plurality of different locations.

9. The method of claim 1, wherein said designating the two or more connected regions is performed automatically by the processor.

10. The method of claim 1, wherein said designating the two or more connected regions is performed semi-automatically by the processor in response to at least one user input designating at least one of one of the two or more connected regions or a border between two of the two or more connected regions.

11. The method of claim 1, wherein said designating the two or more connected regions, said generating the modified ultrasound image and said causing the display device to display the modified ultrasound image are performed retrospectively after the acquisition of the ultrasound video data.

12. The method of claim 1, wherein said designating the two or more connected regions, said generating the modified ultrasound image and said causing the display device to display the modified ultrasound image are performed in near real-time during the process of said acquiring the ultrasound video data.

13. An ultrasound imaging system comprising:
    an ultrasound probe;
    a display device; and
    a processor in electronic communication with the ultrasound probe and the display device, wherein the processor is configured to:
        control the ultrasound probe to acquire ultrasound video data of an anatomical region while an external force is being applied to induce movement within the anatomical region, where the ultrasound video data comprises a plurality of ultrasound images;
        designate two or more connected regions and a boundary between the two or more connected regions in one of the plurality of ultrasound images, the two or more connected regions including a first connected region and a second connected region, where each of the two or more connected regions represents an interconnected tissue group that moves as a unit in response to the external force;
        automatically generate a modified ultrasound image based on the one of the plurality of images by graphically distinguishing the first connected region from the second connected region; and
        cause the display device to display the modified ultrasound image,
    wherein the first connected region is an anterior rectal wall of the anatomical region and the second connected region is a posterior vaginal wall of the anatomical region.

14. The ultrasound imaging system of claim 13, wherein the processor is configured to generate the modified ultrasound image by color-coding each of the two or more connected regions with a different color to graphically distinguish the first connected region from the second connected region.

15. The ultrasound imaging system of claim 13, wherein the processor is configured to generate the modified ultrasound image by adding a boundary line between the first connected region and the second connected region.

16. The ultrasound imaging system of claim 15, wherein the boundary line includes a plurality of color-coded segments in order to indicate an amount of relative motion between the first connected region and the second connected region.

17. The ultrasound imaging system of claim 13, wherein the processor is configured to implement a machine-learning model to designate the two or more connected regions.

18. The ultrasound imaging system of claim 13, wherein the processor is configured to analyze at least two of the plurality of images in order to designate the two or more connected regions in the one of the plurality of ultrasound images.

19. The ultrasound imaging system of claim 13, wherein the processor is configured to determine a direction of motion between the first connected segment and the second connected segment for a plurality of different locations and perform at least one of:
using color to indicate the direction of motion for the plurality of different locations; or
displaying a plurality of icons on the modified image to indicate the direction of motion for the plurality of different locations.

20. The ultrasound imaging system of claim 13, wherein the processor is configured to designate the two or more connected regions semi-automatically after receiving at least one user input designating at least one of the two or more connected regions or a border between the two or more connected regions.

21. The method of claim 1, wherein the external force is varied so there are periods of increasing force and periods of decreasing force during the acquisition of the ultrasound video data.

22. The ultrasound imaging system of claim 13, wherein the external force is varied so there are periods of increasing force and periods of decreasing force during the acquisition of the ultrasound video data.

* * * * *